(12) United States Patent
Schweikert

(10) Patent No.: US 8,343,091 B2
(45) Date of Patent: Jan. 1, 2013

(54) SECURITY TIP FOR VASCULAR CATHETER AND METHOD OF USING SAME

(75) Inventor: Timothy M. Schweikert, Levittown, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 13/285,349

(22) Filed: Oct. 31, 2011

(65) Prior Publication Data

US 2012/0071861 A1  Mar. 22, 2012

Related U.S. Application Data

(62) Division of application No. 11/429,814, filed on May 8, 2006, now Pat. No. 8,048,059.

(60) Provisional application No. 60/679,098, filed on May 9, 2005.

(51) Int. Cl.
*A61M 1/00* (2006.01)
(52) U.S. Cl. .......................... 604/28; 604/508
(58) Field of Classification Search .............. 604/28–45, 604/288.01–288.04, 500–522
See application file for complete search history.

(56) References Cited

U.S. PATENT DOCUMENTS

| | | | |
|---|---|---|---|
| 3,020,913 A | 2/1962 | Heyer | |
| 4,434,810 A | 3/1984 | Atkinson | |
| 4,701,166 A | 10/1987 | Groshong et al. | |
| 4,753,640 A | 6/1988 | Nichols et al. | |
| 4,892,518 A * | 1/1990 | Cupp et al. | 604/288.02 |
| 5,112,301 A | 5/1992 | Fenton, Jr. et al. | |
| 5,160,325 A | 11/1992 | Nichols et al. | |
| 5,554,136 A | 9/1996 | Luther | |
| 5,810,789 A | 9/1998 | Powers et al. | |
| 5,827,237 A | 10/1998 | Macoviak et al. | |
| 6,293,958 B1 | 9/2001 | Berry et al. | |
| 6,743,218 B2 | 6/2004 | Maginot et al. | |
| 6,808,510 B1 | 10/2004 | DiFiore | |
| 2004/0156908 A1 * | 8/2004 | Polaschegg | 424/486 |

FOREIGN PATENT DOCUMENTS

WO  03045464 A2  6/2003

OTHER PUBLICATIONS

Review of Hemodialysis for Nurses and Dialysis Personnel, "Anticoagulation and Heparin Administration" S. Hansen et al. pp. 134-136 (dateunknown).
International Search Report dated Jan. 22, 2007, PCT/US06/17722 (3 pages).
Written Opinion dated Jan. 22, 2007, PCT/US06/17722 (3 pages).
European Search Report dated May 7, 2010; European Application No. EP 06759315.2 (6 pages).
Office Action dated May 24, 2011; corresponding Japanese Application No. 2008-511238 (5 pages); translation.

* cited by examiner

*Primary Examiner* — Kevin C Sirmons
*Assistant Examiner* — Phillip Gray
(74) *Attorney, Agent, or Firm* — Glenn M. Massina, Esq.; Fox Rothschild LLP

(57) ABSTRACT

A method of maintaining a locking fluid in an implanted catheter including positioning a catheter assembly in a patient, the catheter assembly including a first lumen having a closed first distal end and a first proximal end, and a second lumen having a closed second distal end and a second proximal end and injecting the locking fluid into the first and second proximal ends at a low pressure such that the locking fluid enters each lumen without opening the respective closed distal end. A method of withdrawing the locking fluid is also provided.

5 Claims, 4 Drawing Sheets

SECURITY TIP FOR VASCULAR CATHETER AND METHOD OF USING SAME

CROSS REFERENCE TO RELATED APPLICATIONS

The present application claims the benefit of U.S. Provisional Patent Application Ser. No. 60/679,098, filed May 9, 2005, and claims priority from U.S. patent application Ser. No. 11/429,814, filed May 8, 2006, both of which applications are incorporated herein in their entirety.

FIELD OF THE INVENTION

This relates to the field of medical devices and more particularly to catheters and catheter assemblies.

BACKGROUND OF THE INVENTION

Hemodialysis catheters are implanted into the vasculature of a patient, and have proximal ends that extend from the patient and are connectable to and disconnectable from tubing of a hemodialysis apparatus. Such catheters are provided with a first lumen and a second lumen coextending to respective distal tips that are carefully positioned at a selected site in a particular vessel of the patient, so that undialysed blood may be withdrawn from the patient's vessel while dialysed blood may be reintroduced into the patient's vessel simultaneously, at respective distal tip openings of the lumens. The catheter lumens may be coextending separate catheters or may be dual lumens of a single catheter separated by a septum wall. The distal tips of the two lumens are generally staggered along the vessel such that blood being withdrawn does not include any significant amount of dialysed blood that has been reintroduced into the vessel at the more distal of the two distal tips.

When a particular dialysis procedure has been completed, the proximal ends of the catheter are disconnected from the tubes of the hemodialysis apparatus, and the lumens are generally inactive until the subsequent dialysis procedure, although fluid medication or saline may be infused into at least one of the lumens, if and when desired, or a blood sample withdrawn. However, blood is highly susceptible to coagulation and clot formation. The addition of a specific agent or locking solution to the catheter or any extracorporeal blood-contacting surface can reduce the incidence of coagulation by interfering and/or inhibiting the hematological chemistry of blood and its interaction with synthetic materials, such as those from which catheters are made.

It is conventional, then, to introduce anticoagulant locking solutions such as heparin into an implanted catheter between hemodialysis treatments, to prevent clotting of blood within the catheter, and which then is withdrawn for the subsequent dialysis procedure. The blood pressure of the patient effectively maintains the locking solution within the catheter lumens by producing a pressure gradient against the locking solution, even though the distal lumen tips are open structures. However, certain amounts of locking solution are known to enter the patient's blood stream through the open distal tips. The amounts introduced into the patient are not at a level to cause toxicity or disrupt a patient's hematology.

It is desired to provide a catheter that will minimize or eliminate the small amounts of locking solution entering a patient's blood stream from an implanted catheter between dialysis treatments.

SUMMARY OF THE INVENTION

The catheter of the present invention includes a first lumen having a first distal tip, and a second lumen having a second distal tip, wherein the first and second distal tips having wall sections that are normally disposed in a closed position but are each openable under fluid pressure. While both lumens have openable distal tip wall sections, the first distal tip has a wall section openable both inwardly and outwardly when the first lumen is subjected to negative pressure and positive pressure, respectively, relative to the blood pressure of the patient in whom the catheter has been implanted; but the second distal tip has a wall section openable only outwardly, that is, when the second lumen is subjected to positive pressure, and that closes when the second lumen is subjected to negative pressure.

In a preferred embodiment, the first lumen includes a flap section that is joined at a connected section to the wall of the first lumen and extends to a free end that extends to the opposite side of the first lumen to close the first distal tip when undeflected; the flap section is deflectable to open into the first lumen under negative pressure applied to the proximal end of the first lumen, and is deflectable to open outwardly from the first lumen under positive pressure applied to the proximal end of the first lumen.

The second lumen extends a selected distance distally of the first distal tip to a second distal tip that is a generally rounded tip when closed, and the second distal tip is defined by an openable section that is internally concave and may be formed by at least one slit cut into a closed rounded distal tip after extrusion of the lumen, defining at least two generally curved lip portions. The several lip portions are openable outwardly under positive pressure applied to the distal end of the second lumen, and a closable together under negative pressure applied to the second lumen. Near the second distal tip, in the side wall of the second lumen are one or more openable side port sections that are openable inwardly upon application of negative pressure to the proximal end of the second lumen.

The closable and openable sections of the first and second distal tip sections of the first and second lumens operate thusly: during hemodialysis, negative pressure is applied to the first lumen and blood is drawn from a patient's vessel into the first distal tip and through the first lumen; positive pressure applied to the second lumen when blood enters the proximal end of the second lumen and separates the several lip portions at the second distal tip to re-enter the vessel. Were the reverse of the pressures to be caused by an incorrect hemodialysis connection, blood traveling into the first lumen would open the flap to enter the vessel, while negative pressure on the second lumen would close the several lip sections but open the side ports for blood to enter from the vessel. Between dialysis procedures, locking solution injected under low pressure into the catheter would fill both lumens since the distal tips would be in their closed, undeflected conditions, and when removed, blood from the vessel would enter both distal tips due to negative pressure on both lumens.

The present invention also includes a method for maintaining a locking fluid in an implanted catheter; comprising the steps of: providing a catheter having a first lumen having a closed openable first distal end and a first proximal end, and a second lumen having a closed openable second distal end and a second proximal end; and injecting locking fluid into the first and second proximal ends, wherein the closed first and second distal ends retain the locking fluid in the first and second lumens. The present invention also includes a method of removing a lock solution from a catheter, comprising the steps of: providing a catheter having a first lumen having a closed openable first distal end and a first proximal end, and a second lumen having a closed second distal end and a second proximal end, and at least one closed openable side port disposed proximal of the second distal end; withdrawing the lock solution from the first proximal end, wherein the first distal end opens to allow blood into the first lumen; and, withdrawing the lock solution from the second proximal end, wherein the at least one flap opens to allow blood into the second lumen

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
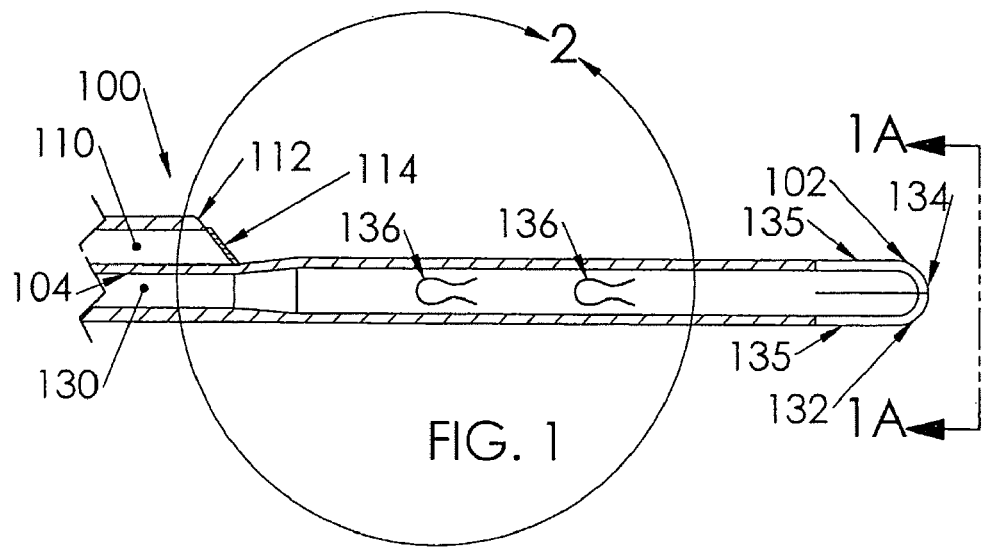
FIG. 1 is a side view, in section, of a distal end of a catheter according to a first embodiment of the present invention.

In the drawings, like numerals indicate like elements throughout. Certain terminology is used herein for convenience only and is not to be taken as a limitation on the present invention. The term "distal" in meant to describe the portion of a catheter according to the present invention that is inserted into a patient, and the term "proximal" is meant to describe the portion of a catheter according to the present invention that remains exterior of the patient. The terminology includes words specifically mentioned, derivatives thereof, and words of similar import. The following describes preferred embodiments of the invention. However, it should be understood based on this disclosure, that the invention is not limited by the preferred embodiments described herein.

Referring now to FIG. 1, a catheter 100 according to a first embodiment of the present invention is shown. The catheter 100 is a dual lumen catheter used for hemodialysis, wherein a first lumen 110 is used to draw blood from a vessel, such as the internal jugular vein, and a second lumen 130 is used to return blood to the vessel. Further, while the second lumen 130 is used to return blood to the vessel, the second lumen 130 may also be used to administer other fluids, such as medication, to the vessel.

One inventive aspect of the present invention is the distal end 102 of the catheter 100. Consequently, the proximal end of the catheter 100, which typically includes: a hub at the proximal ends of the first and second lumens 110, 130; a pair of extension tubes extending proximally from the hub, such that each extension tube is in fluid communication with one of the first and second lumens 110, 130 through the hub; and a luer connector on a proximal end of each of the extension tubes, is not shown, as the proximal end of the catheter 100 is known to those skilled in the art.

Figure 1A:
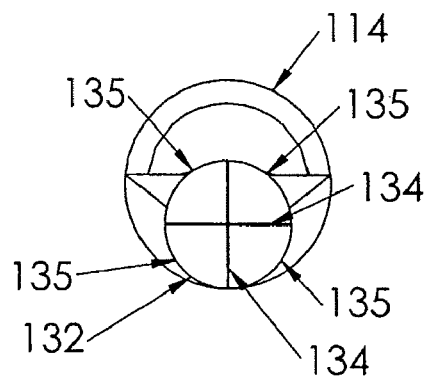
FIG. 1A is a distal end profile view, in section, of the catheter taken along lines 1A-1A of FIG. 1.

As seen in FIG. 1A, the first lumen 110 preferably has a D-shaped cross section and the second lumen 130 preferably has a circular cross section. However, those skilled in the art will recognize that the cross sections may be other shapes, such as "Double D", "Circle C", or other lumen cross section configurations known to those skilled in the art.

A cross-sectional view of the distal end 102 of the catheter 100 is shown in FIG. 1. The first and second lumens 110, 130 are adjacent to and parallel to each other, and are separated from each other by a septum 104. The second lumen 130 extends more distally than the first lumen 110. The first and second lumens 110, 130 provide a smooth outer surface for insertion into a patient's blood vessel.

Figure 2:
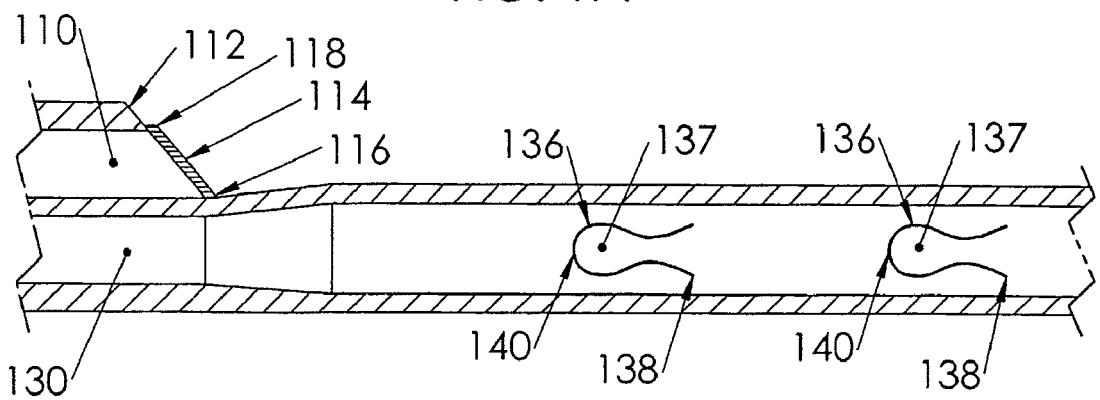
FIG. 2 is an enlarged portion of the catheter taken along oval 2 of FIG. 1.

The distal end 112 of the first lumen 110 is enlarged in FIG. 2. The distal end 112 includes a flap 114 that extends obliquely from a connected distal portion 116 to a free proximal portion 118. The flap 114 closes the distal end 112 of the first lumen 110 to restrict fluid flow into or out of the first lumen 110. The connected distal portion 116 is sufficiently pliable to allow the flap 114 to pivot about the distal portion 116 to open the first lumen 110 during use, such as when blood is either being drawn into the first lumen 110 or when blood is being expelled from the first lumen 110.

Referring back to FIGS. 1 and 1A, the second lumen 130 includes an internally concave, generally dome-shaped tip or distal end 132 that is generally closed, but with a plurality of slits 134 extending along wall sections of the second distal end, the slits being arranged, for example, as at least one pair of opposed slits generally bisecting the second distal portion and extending proximally from the distal tip 132, whereby bisected or slit-divided portions of the second distal tip are movable apart allowing the distal end 132 to open under pressure from the second lumen 130 such that the second distal end is a valve. Slits 134 are shown in FIGS. 1 and 1A arranged as two pairs of opposing slits. A generally curved lip portion 135 is formed between each slit 134. As seen in FIG. 1A, four lip portions 135 are formed, although those skilled in the art will recognize that more or less than four lip portions 135 may be formed. The shape of the distal end 132 and the cut of the slits 134 allow fluid flow from the second lumen 130, through the distal end 132 and out of the second lumen 130, but restrict fluid flow into the second lumen 130 from the distal end 132.

A plurality of side ports 136 are formed in the walls of the second lumen 130 proximal of the distal end 132, with a flap 137 covering each side port 136. Each flap 137 is preferably generally bulbous-shaped, with a distal connected end 138 and a free proximal end 140. In an unpressurized condition, each flap 137 closes off its respective side port 136 to restrict fluid flow through the side port 136 by being disposed within the thickness of the wall section. It may also be seen that the second distal end portion, the second distal tip 132 and the second movable portions 135 are formed to be integral with the wall section of the second lumen 130 that has a generally constant thickness.

To manufacture the catheter 100, it is preferred that the lumens 110, 130 are co-extruded according to procedures well known to those skilled in the art. The distal end 102 is inserted into a tipping machine that forms the flap 114 over the distal end 112 of the first lumen 110 and forms the internally concave distal end 132 of the second lumen 130. The flap 114 is then die cut to separate the free end 118 of the flap 114 from the distal end and to allow the flap 114 to rotate about the connected end 116. The slits 134 are also cut to form the lip portions 135 in the distal end 132 of the second lumen 130. The flaps 137 are also die cut to separate the free end 140 of each flap 137 from the wall of the second lumen 130.

In operation, the catheter 100 is inserted into the patient's blood vessel according to techniques well known to those skilled in the art. When the proximal end of the catheter 100 is connected to an exterior device, such as a hemodialysis machine (not shown), blood flows from the vessel, through the catheter 100, to the exterior device, back through the catheter 100, and into the vessel again.

Figure 3:
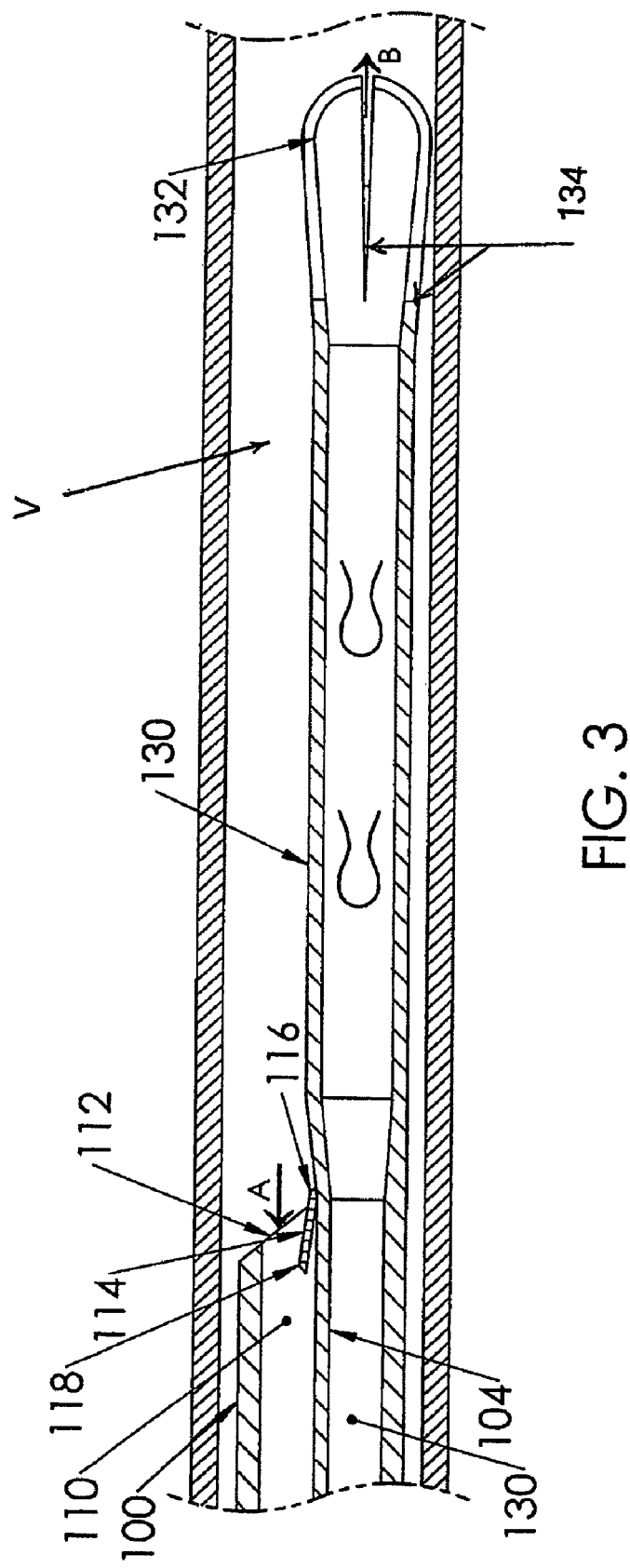
FIG. 3 is an enlarged distal end profile view, in section, of the catheter being operated in normal operation.

When the catheter 100 is correctly connected to the exterior device, standard operation of the catheter 100 is shown schematically in FIG. 3. Blood is drawn from the vessel V into the distal end 112 of the first lumen 110 along the direction of arrow "A". Blood pressure acting on the flap 114 pivots the flap 114 about the connected end 116 so that the free end 118 travels generally proximally, opening the distal end 112 and allowing the blood to flow into the first lumen 110. The blood then travels to the exterior device, where the blood is processed.

The processed blood is then transported to the second lumen 130, where the blood enters the proximal end of the second lumen 130 and travels through the second lumen 130 to the distal end 132 of the second lumen 130. The pressure of the flowing blood against the distal end 132 of the second lumen 130 separates the lip portions 135 from each other, opening the distal end 132, and allowing the blood to exit the second lumen 130 along the direction of arrow "B".

Figure 4:
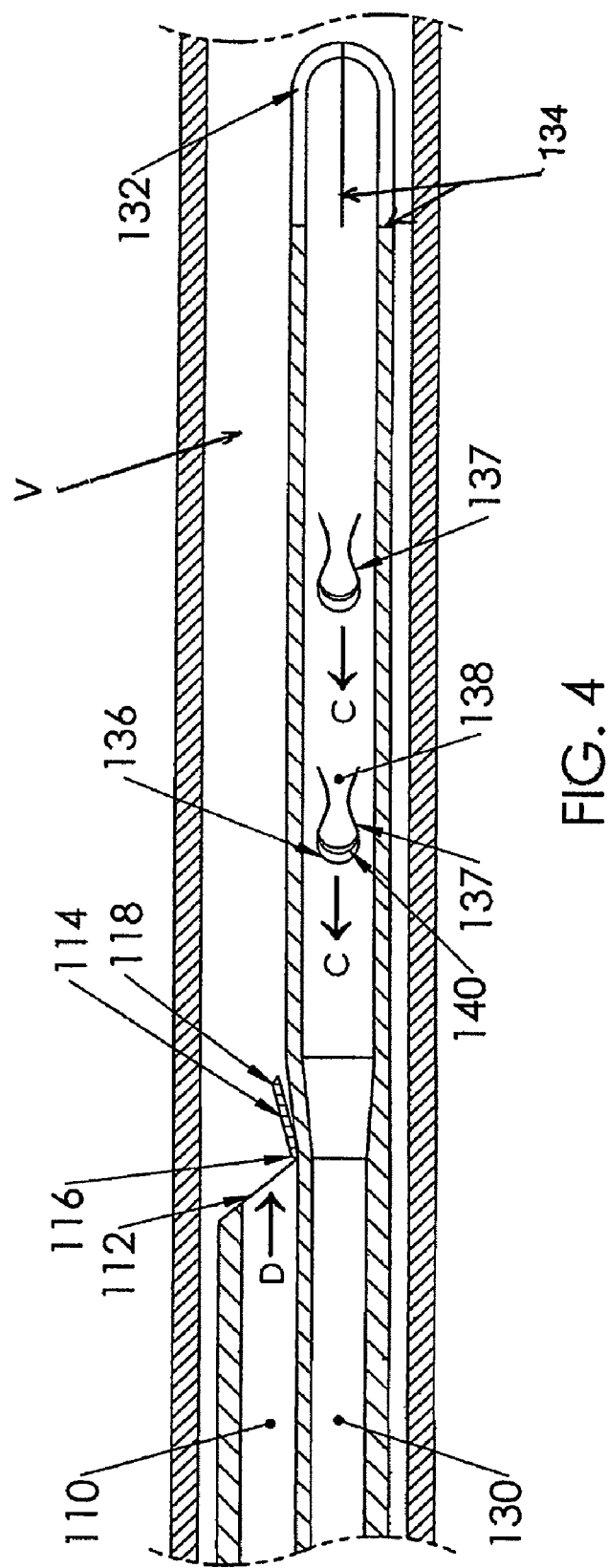
FIG. 4 is an enlarged distal end profile view, in section, of the catheter being operated in reverse operation.

Occasionally, however, the catheter 100 may be incorrectly connected to the exterior device such that blood is drawn into the second lumen 130 and discharged through the first lumen 110. Operation of the catheter 100 in this manner is shown schematically in FIG. 4. Blood is drawn into the vessel V into the second lumen 130 through the flaps 137 in the distal end 132 of the second lumen 130, as shown by the arrows "C" in FIG. 4. The flaps 137 open into the second lumen 130 to allow blood to be drawn from the vessel V into the second lumen 130. The blood then travels to the exterior device, where the blood is processed.

The processed blood is then transported to the first lumen 110, where the blood enters the proximal end of the first lumen 110 and travels through the first lumen 110 to the distal end 112 of the first lumen 110 to the flap 114. Blood pressure acting on the flap 114 pivots the flap 114 about the connected end 116 so that the free end 118 travels generally distally, opening the distal end 112 and allowing the blood to flow back into the vessel V, as indicated by arrow "D".

In between treatments, when blood is not flowing through the catheter 100, a catheter lock solution is injected into each of the first and second lumens 110, 130 from the proximal end of each of the first and second lumens 110, 130. Regarding the first lumen 110, the flap 114 biases toward the closed position to close the distal end 112 of the first lumen 110 and prevent the lock solution from dispersing from the first lumen 110 into the vessel V. Regarding the second lumen 130, the lip portions 135 bias toward a closed position to close the distal end 132, and the flaps 137 bias toward the wall of the second lumen 130 to close the flaps 137 to prevent the lock solution from dispersing from the second lumen 130 into the vessel V.

To prepare the catheter 100 for a subsequent treatment, a syringe (not shown) is connected to the proximal end of the first lumen 110 and the lock solution is vacuum drawn from the first lumen 110 into the syringes. The flap 114 biases toward the open position to allow blood into the distal end 112 of the first lumen 110 to make up for the now-depleted lock solution. The syringe (or a subsequent syringe) is connected to the proximal end of the second lumen 130 and the lock solution is vacuum drawn from the second lumen 130 into the syringe. The flaps 137 open to allow blood into the distal end 132 of the second lumen 130 to make up for the now-depleted lock solution. The syringe is removed and the proximal end of the catheter 100 is able to be connected to a hemodialysis machine.

Figure 5:
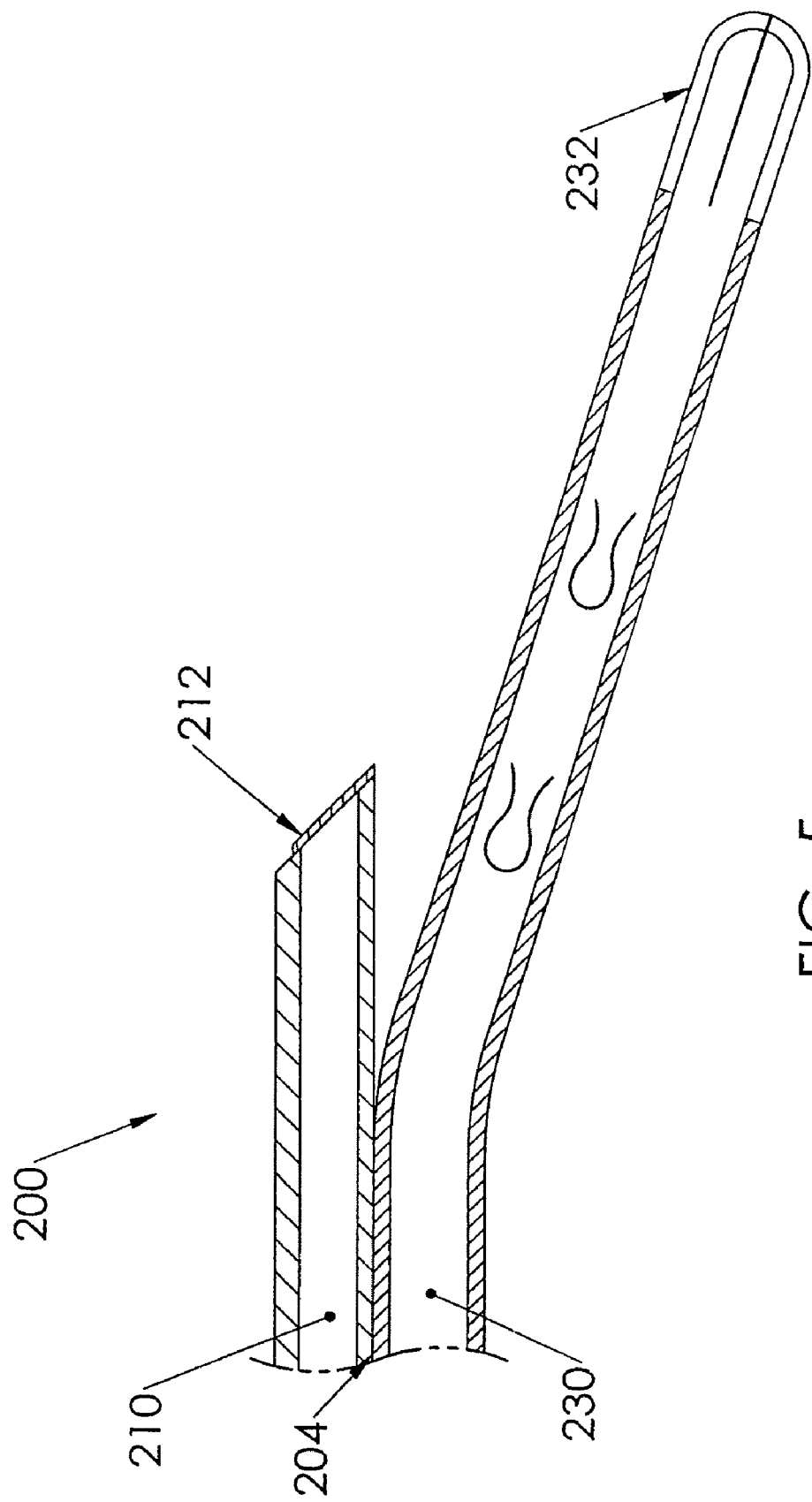
FIG. 5 is an enlarged distal end profile view, in section, of a catheter according to a second embodiment of the preferred invention.

In an alternate embodiment, shown in FIG. 5, a catheter 200 includes a first lumen 210 and a second lumen 230 that have distal ends 212, 232, respectively, that are split apart from each other. A septum 204 that divides the first lumen 210 from the second lumen 230 splits off at a predetermined location to allow the distal end 212 of the first lumen 210 to separate from the distal end 232 of the second lumen 230.

Optionally, as will be recognized by those skilled in the art, the septum 204 may be splittable such as by being constructed to have two layers initially joined to each other as shown in FIG. 5, to allow the distal end 212 of the first lumen 210 to be split away from the distal end 232 of the second lumen 230 at a variable location, as determined by the inserting physician during insertion of the catheter into the patient.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of maintaining and removing a locking fluid in an implanted catheter comprising:
   positioning a catheter assembly in a patient, the catheter assembly including a first lumen having a first distal end and a first proximal end with the first distal end including a two-way valve at a distal tip thereof, and a second lumen having a second distal end and a second proximal end with the second distal end extending distally beyond the first distal end and including a one-way valve at a distal tip thereof and at least one side port extending through the second lumen proximally of the distal tip;
   injecting the locking fluid into the first and second proximal ends at a low pressure such that the locking fluid enters each lumen without opening the respective closed distal end;
   withdrawing the locking fluid from the first proximal end with a first force such that the two-way valve opens to allow blood into the first lumen; and
   withdrawing the locking fluid from the second proximal end with a second force such that the at least one side port opens to allow blood into the second lumen.

2. The method of claim 1 wherein the catheter is utilized for hemodialysis treatment and blood is passed through the first and second lumens at a pressure higher than the low pressure.

3. The method of claim 2 wherein the first lumen is utilized to withdraw blood from the patient and the second lumen is utilized to return blood to the patient.

4. The method according to claim 1 wherein the first and second forces are equal.

5. The method according to claim 1 wherein each of the withdrawing steps is performed via a syringe.

* * * * *